(12) United States Patent
Bernard et al.

(10) Patent No.: US 12,076,029 B2
(45) Date of Patent: *Sep. 3, 2024

(54) MONOBLOC ACETABULAR REAMER SECTION

(71) Applicant: Incipio Devices SA, St-Blaise (CH)

(72) Inventors: Lionel Bernard, Bonnétage (FR);
Fabrice Chenaux, Cortaillod (CH);
Antonio Fiorentini, Fontaines (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/864,436

(22) Filed: Jul. 14, 2022

(65) Prior Publication Data

US 2023/0310010 A1 Oct. 5, 2023

Related U.S. Application Data

(63) Continuation-in-part of application No. 16/622,327, filed on Dec. 13, 2019, now Pat. No. 11,419,615.

(51) Int. Cl.
*A61B 17/16* (2006.01)
*A61B 17/00* (2006.01)

(52) U.S. Cl.
CPC ...... *A61B 17/1666* (2013.01); *A61B 17/1637* (2013.01); *A61B 2017/00526* (2013.01)

(58) Field of Classification Search
CPC ................................................ A61B 17/1666
See application file for complete search history.

(56) References Cited

U.S. PATENT DOCUMENTS

| 8,679,124 B2* | 3/2014 | Lechot | A61B 17/1617 606/81 |
| 2002/0141837 A1* | 10/2002 | Feld | B23B 51/00 408/231 |

FOREIGN PATENT DOCUMENTS

DE 202010005376 * 8/2010 ............. A61B 17/16

* cited by examiner

*Primary Examiner* — Christian A Sevilla
(74) *Attorney, Agent, or Firm* — Da Vinci Partners LLC; John Moetteli

(57) ABSTRACT

A system, method and/or reamer driver device is provided having a domed external surface and a domed internal surface being concentric to the domed external surface thereby defining a hollow dome or section thereof. At least one cutting tooth is disposed on the hollow dome or section thereof. The cross-sectional thickness T measured substantially perpendicular to the crest of the at least one tooth is greater than the radial distance t between the external and internal domed surfaces. The hollow dome or section thereof is made using an injection molding process or a 3D printing process.

14 Claims, 13 Drawing Sheets

MONOBLOC ACETABULAR REAMER SECTION

CROSS REFERENCE TO RELATED APPLICATIONS

This application is a Continuation-in-Part (CIP) of the National Stage Ser. No. 16/622,327 filed Dec. 13, 2019 of the PCT Application No. PCT/IB2018/000706, filed Jul. 2, 2018, which claims benefit of U.S. provisional patent application Ser. No. 62/527,088, filed Jun. 30, 2017, entitled MONOBLOC ACETABULAR REAMER, the contents of which are explicitly incorporated herein by reference and relied upon to define features for which protection may be sought hereby as it is believed that the entirety thereof contributes to solving the technical problem underlying the invention, some features that may be mentioned hereunder being of particular importance.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein are to be construed as an admission that the present invention is not entitled to antedate such material by virtue of prior invention.

BACKGROUND OF THE INVENTION

This invention relates to a reamer for cutting the acetabulum, in preparation for receiving an acetabular implant, and processes or methods of manufacturing thereof.

Current reamers are stamped of metal and then drilled to create cutting edges. The stamping process, however, creates recesses into which bone and soft tissue matter can become trapped, making cleaning difficult. In addition, accuracy and precision of the reamer is often difficult to obtain by stamping.

There exists a need for a reamer which is easier to clean. In addition, there exists a need for a reamer that is precise and easier to manufacture.

SUMMARY OF THE INVENTION

The acetabular reamer of the invention meets these needs via a reamer driver device having typically a domed external surface and a domed internal surface being concentric to the domed external surface thereby defining a hollow dome. At least one cutting tooth is disposed on the hollow dome. The cross-sectional thickness T measured substantially perpendicular to the crest of the at least one tooth is greater than the radial distance t between the external and internal domed surfaces. The reamer includes a domed internal surface in which a plurality of cutting edge facing surfaces extend completely to the domed internal surface. The cutting edge facing surfaces are formed by drilling or milling. This avoids pockets that trap bone chips or soft tissue and so eases cleaning of the reamer between uses and should improve cutting efficiency as well.

In the preferred embodiment, the reamers of the invention or sections thereof are made by injection molding preferably of metal powder (MIM) and sintering or by using a 3D printing process and sintering or other heat treating. Other materials like plastics, plastics filled with carbon fibers or glass fibers, resins, ceramics can be used as well. The present invention differs from the prior art reamers where teeth are made by deformation of a sheet of metal of constant thickness and where the connecting bars are assembled onto the reamer shell afterwards by a welding process.

The present invention also describes a method of making an acetabular reamer by metal injection molding or by 3D-printing of components that may be sintered and assembled by welding, adhering together typically with epoxy or by ultrasonic bonding. The assembly may optionally then be machined to create the cutting edges and finally optionally heat treated.

BRIEF DESCRIPTION OF THE DRAWINGS

The attached drawings represent, by way of example, different embodiments of the subject of the invention.

Those skilled in the art will appreciate that elements in the Figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT

Figure 1A:
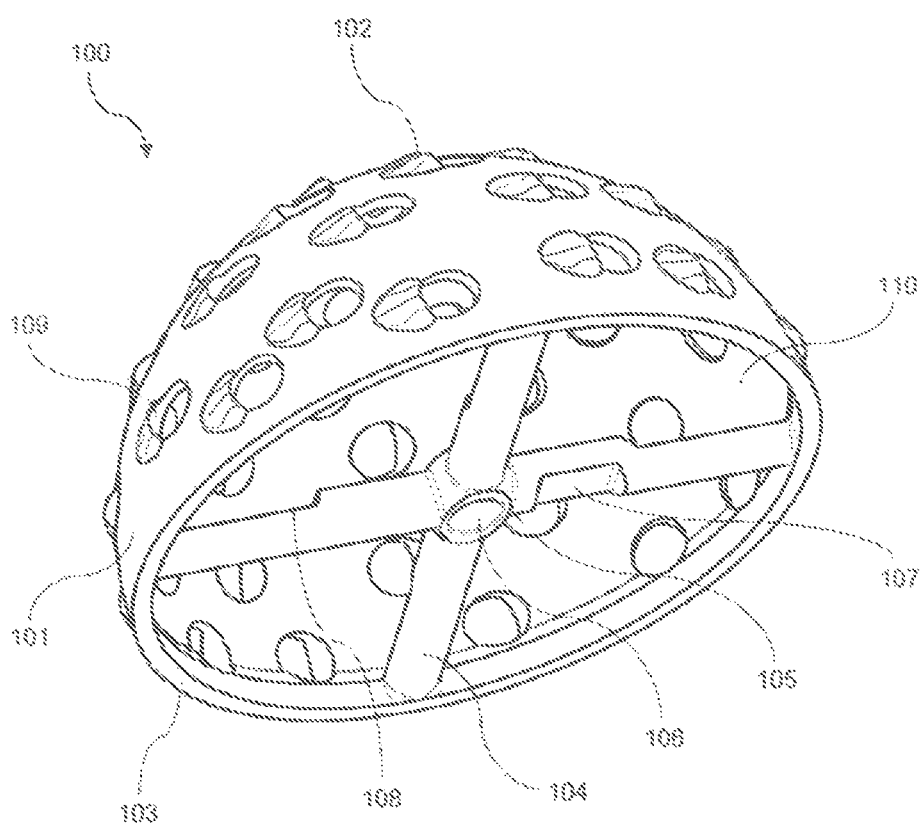
FIG. 1A is a perspective view of the acetabular reamer.
Figure 1B:
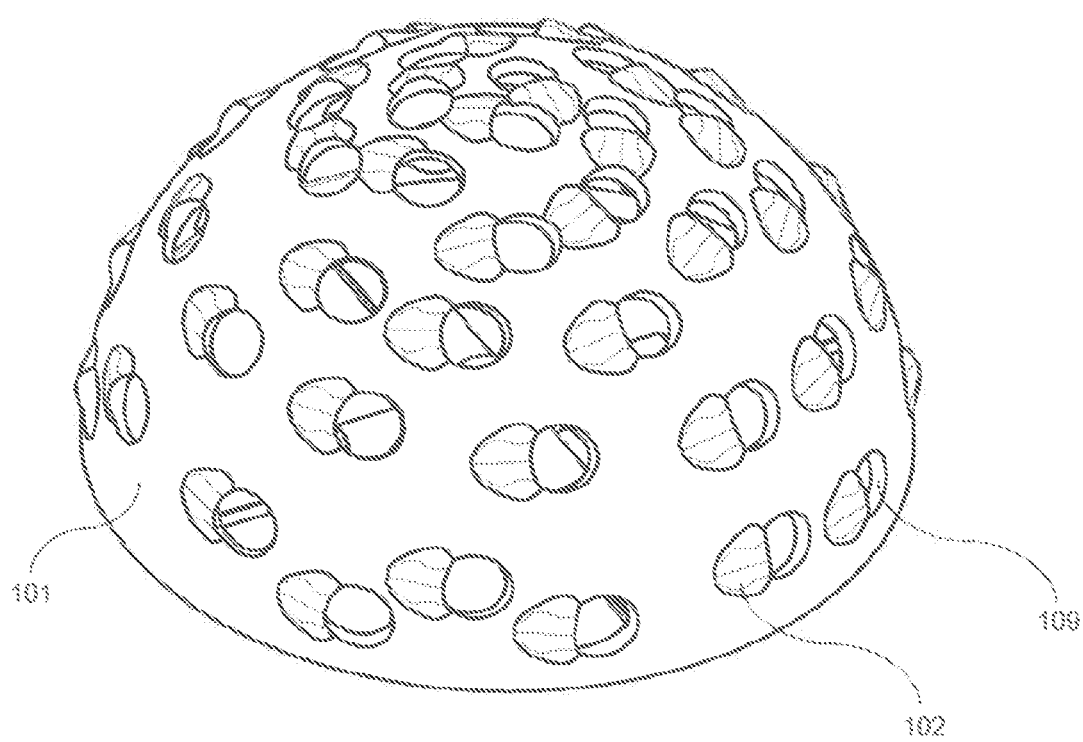
FIG. 1B is another perspective view of the acetabular reamer.

Referring now to FIGS. 1A and 1B, the acetabular reamer 100 is shown after injection molding or 3D-printing and assembling of the components, and as the case may be, sintering and machining of the cutting edges. The acetabular reamer 100 comprises typically a domed external surface 101, a rim 103, and a domed internal surface 110 which together define a hollow dome. The domed external surface and the domed internal surface are concentric with each other and therefore spaced apart by a constant distance. The domed has cutting teeth 102 disposed around the dome to insure an even reaming of a socket when rotated around its main axis. Connecting bars 104 allow the acetabular reamer to be connected to an instrument holder, also called a reamer handle.

Figure 1C:
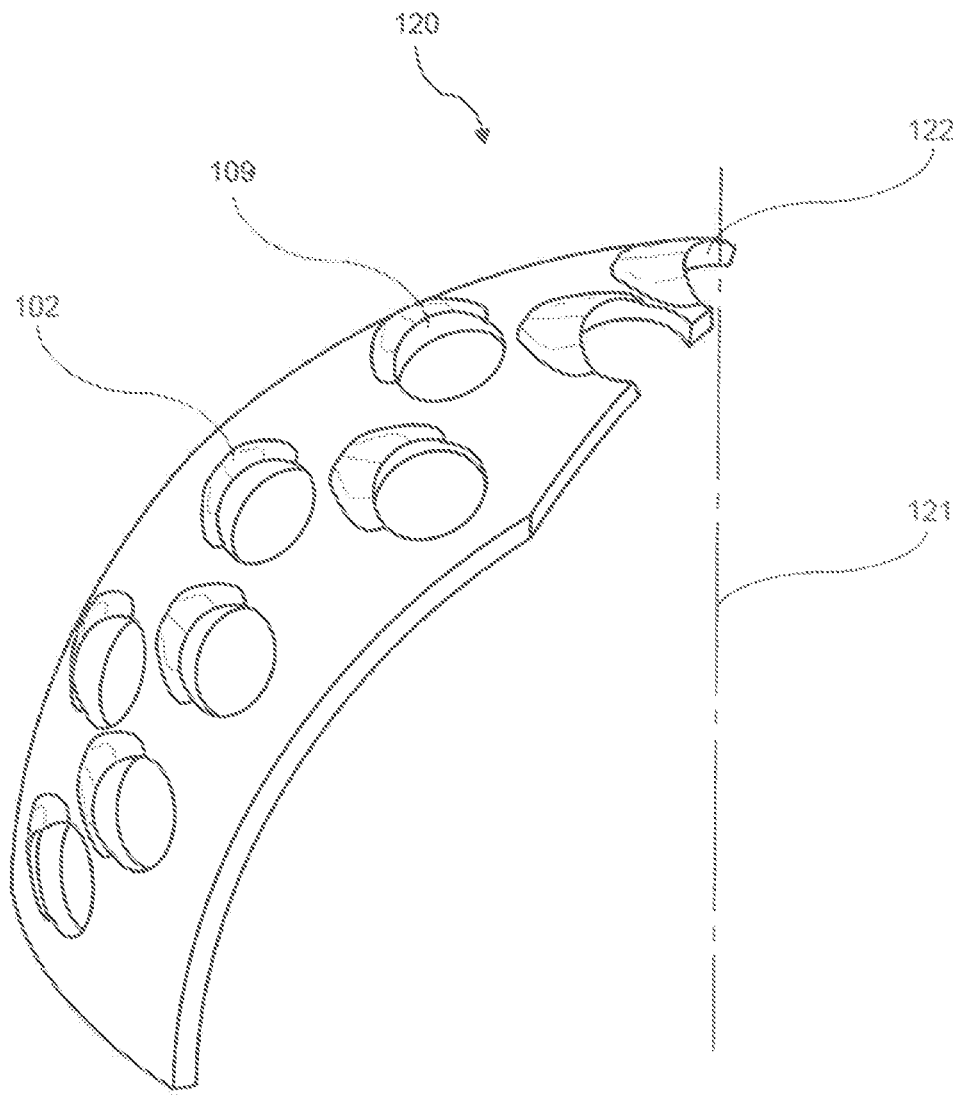
FIG. 1C is a section of a hollow dome forming a cutting blade.
Figure 1D:
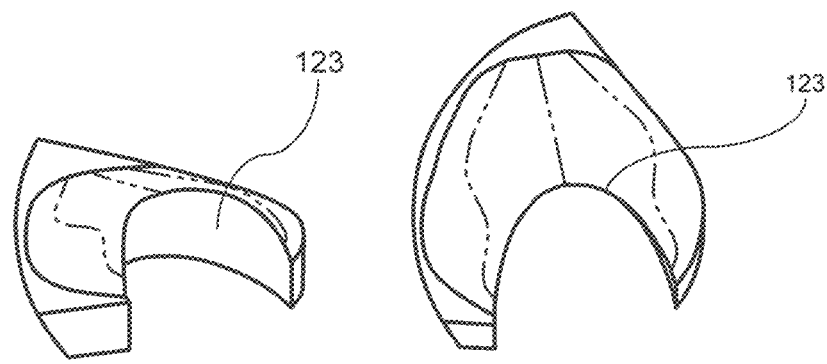
FIG. 1D is an elliptical tooth hole.
Figure 1E:
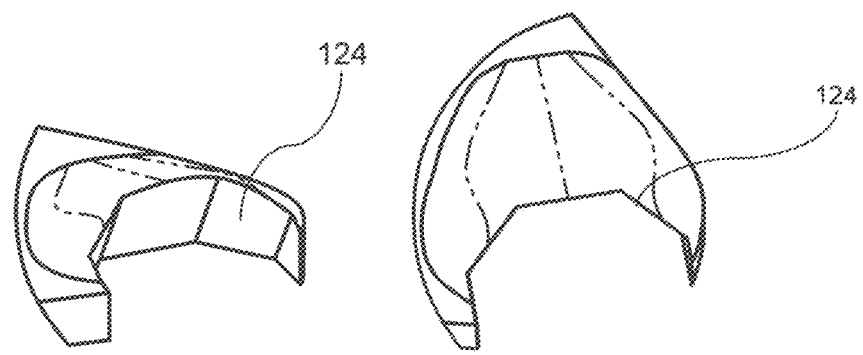
FIG. 1E is a polygonal tooth hole.
Figure 1F:
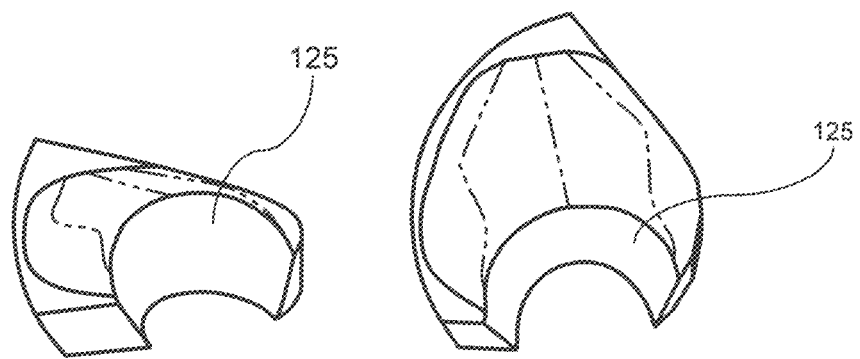
FIG. 1F is a tapered tooth hole.
Figure 1G:
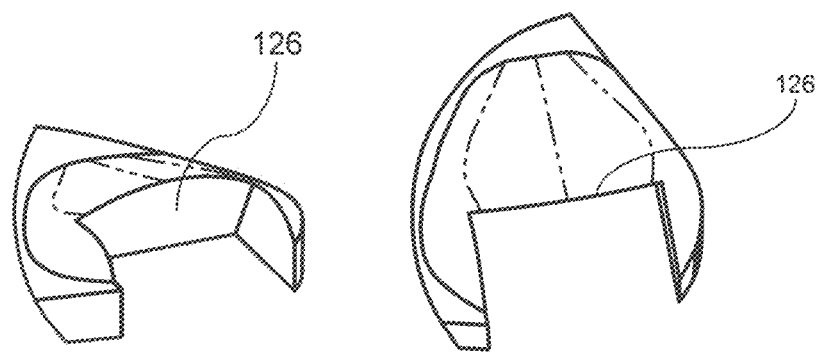
FIG. 1G is a square tooth hole.

Note that although a hollow dome is suitable for the cutting of the acetabulum, many of the benefits of the invention can be obtained using other shapes, depending on the application. A hollow cone or other surface of revolution would also be used in particular applications. A section of a hollow dome forming a cutting blade 120 may also be used to form the cutting tool (see FIG. 1C).

In an embodiment, the four connecting bars are disposed at 90° from each other to form a cross bar. A reinforcement portion 105, having at least one of its cross-section dimensions larger that the diameter of the connecting bars, is located at the center of the cross bars. A hole or opening 106 is located at the center of the cross bar (or the reinforcement portion 105). Undercuts 108 along the connecting bars 104 reduce the cross-section of the connecting bars and decrease the deformation of the rim 103 during any heat treatment (e.g., sintering) process.

In another embodiment, a window 107 along a connecting bar 104 is added for the identification of the size of the reamer.

In another embodiment, the connecting bars 104 are adjacent to the rim 103 of the acetabular reamer and located fully inside the internal surface 110 of the hollow dome. In a different embodiment, the connecting bars may be located above or below the rim 103. In a still further embodiment, the connecting bars have different shapes and cross-section shapes. In fact, the number of connecting bars can be increased or reduced to be adapted to the reamer driver used.

Figure 2:
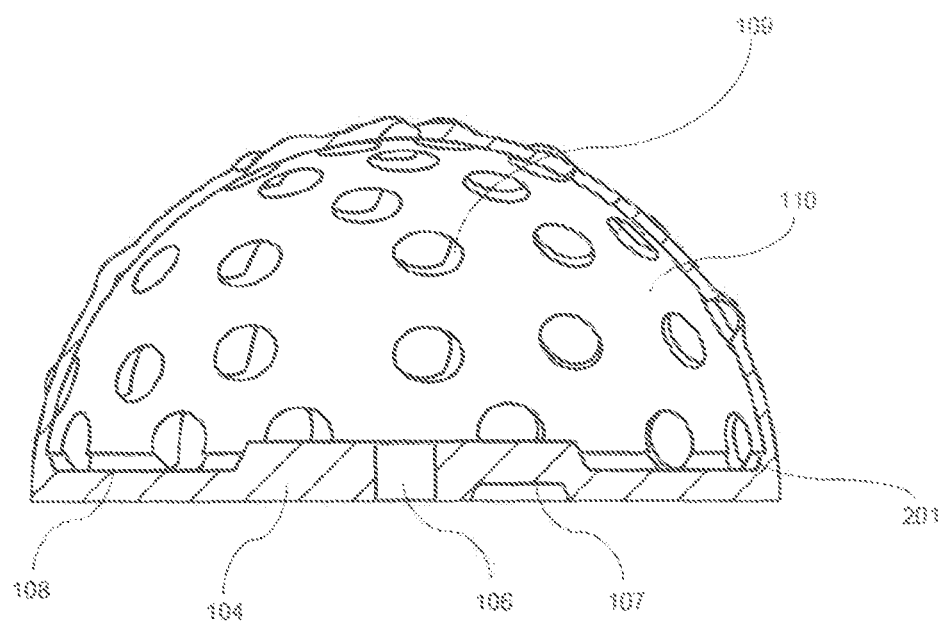
FIG. 2 is a cross-section view of the acetabular reamer.

Now referring to FIG. 2, the domed internal surface 110 has a larger cross-sectional thickness in the equator area, forming a circular reinforcement rim 201.

Figure 3A:
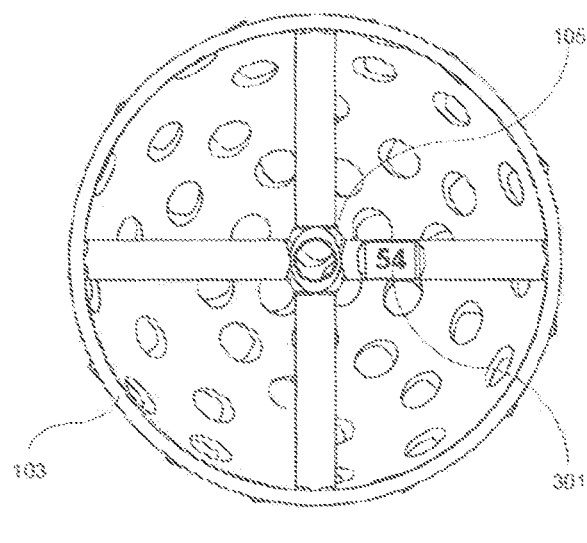
FIG. 3A is a bottom view of the acetabular reamer.

Referring to FIG. 3A, the size of the reamer or any other information 301 can be displayed in the window 107 of the connecting bar.

Figure 3B:
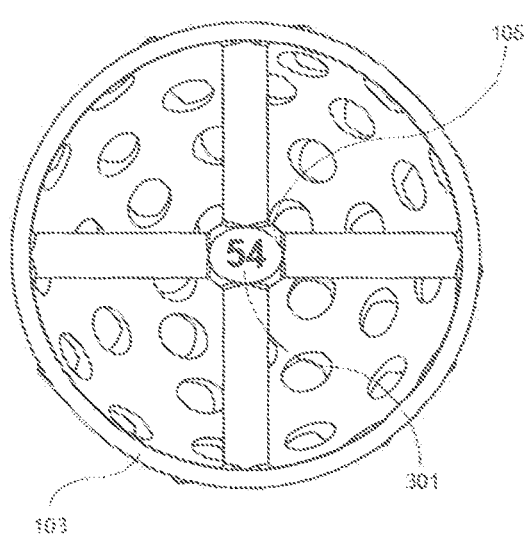
FIG. 3B is a bottom view of a different embodiment of the acetabular reamer.

Referring to FIG. 3B, a different embodiment of the reamer is shown where the center of the cross bar is solid and allows the display of information.

Figure 4:
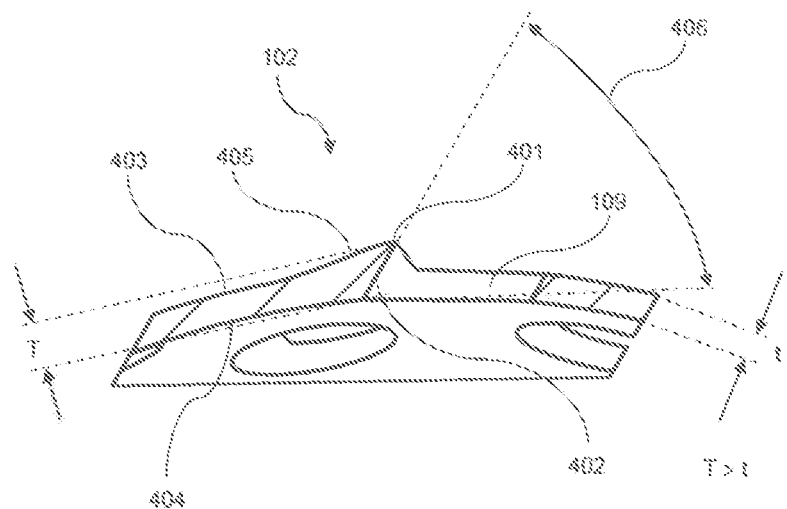
FIG. 4 is a cross-section view of the cutting tooth of the acetabular reamer.

Now referring to FIG. 4, the cross-section of the cutting tooth 102 has a cutting-edge apex 401 on the tooth domed surface or crest 405 which extends from the domed external surface 101, 403. A tooth domed surface or crest 405 is essentially a radial projection of a line centered on a tooth 102 oriented along the cutting trajectory of the tooth and projected onto the top of the tooth. The tooth domed surface or crest 405 connects the tooth external surface 101 to the cutting-edge apex 401. A tooth cutting surface 402 facing the cutting direction is disposed at an angle 406 to the domed internal surface 110, 404. The perpendicular distance t between the external surface 403 and the internal surface 404 is equivalent to the thickness of the reamer hollow dome. The perpendicular distance T between the tooth domed surface 405 and the internal surface 404 is significantly larger than the perpendicular distance t between the external surface 403 and the internal surface 404. Tooth holes 109 are made through the external surface 403, the tooth domed surface 405 and the internal surface 404 to form the cutting edges of the tooth. The tooth holes 109 may be cylindrical, elliptical, polygonal, even square, and/or tapered or have a specific geometry depending on the desired cutting properties. The tooth holes 109 may also comprise only a portion of a cylindrical 122, elliptical 123, polygonal 124, square 126, and/or tapered 125 hole (see FIGS. 1C, ID, 1E, 1F and 1G). The tooth holes 109 are usually oriented at an angle 406 between 90° to 5° from the axis parallel to the surface of the hollow dome. The angle 406 corresponds to what we can refer to herein as the cutting angle of the tooth. Consequently, a 90° angle would be blunt, and a 5° angle would be very sharp considering the direction of cutting.

Figure 5:
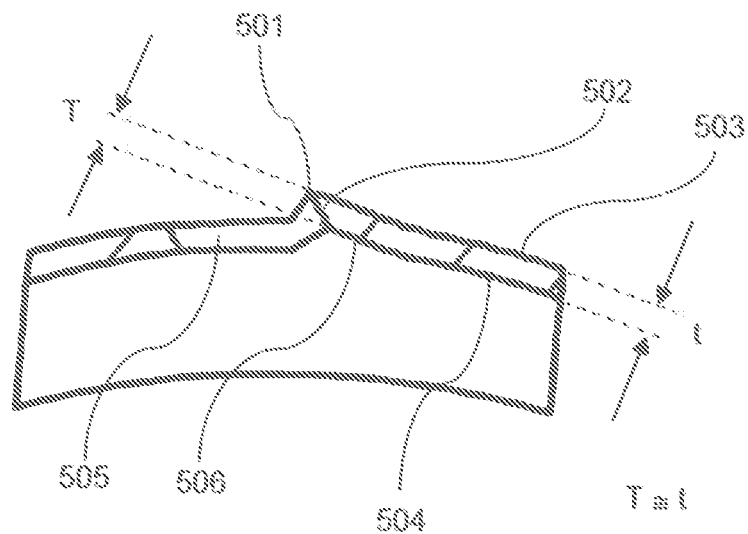
FIG. 5 is a cross-section view of a prior art cutting tooth of an acetabular reamer.

In the prior art tooth shown in FIG. 5, the tooth 500 is formed by deformation of a constant thickness sheet of material. A punching tool is typically usually used to deform the shell and create the tooth geometry. A small cavity 506 is therefore formed on the inside of the shell, which may be problematic when cleaning the acetabular reamer after surgery. It is sometimes difficult to access this cavity 506 for cleaning. The perpendicular distance between the external surface 503 and the internal surface 504 of the hollow dome 100 is essentially equal to the perpendicular distance t between the cutting-edge apex 501 and the tooth internal surface 506. That is because typically, as mentioned above, a sheet metal blank of set thickness is used to form the hollow dome 100.

Referring again to FIG. 4, on the other hand, the tooth 102 of the present invention is not formed by deformation of a constant thickness sheet of material but by injection molding or by 3D-printing. Therefore, the cross-sectional thickness of the tooth 102 is not constant and offers a flat internal domed surface 110 without recesses 506, eliminating bone chip collection areas and thus allowing easier cleaning of the instrument.

Although a single tooth 102 is mentioned, it should be evident that typically, more than one tooth 102 is required to properly cut the acetabulum. In fact many teeth 102, typically formed in a spiral orientation from the apex of the hollow dome 100 to the rim 103, 201 are used. Generally, between 15 and 100 teeth are used on a full hemispherical cutting tool depending on the size of the reamer and the size and geometry of the teeth. The teeth may be oriented in a spiral orientation or disposed in any convenient manner which cuts the desired rotational surface of the dome or other shape when the reamer is rotating thereby cutting the bone evenly.

Figure 6:
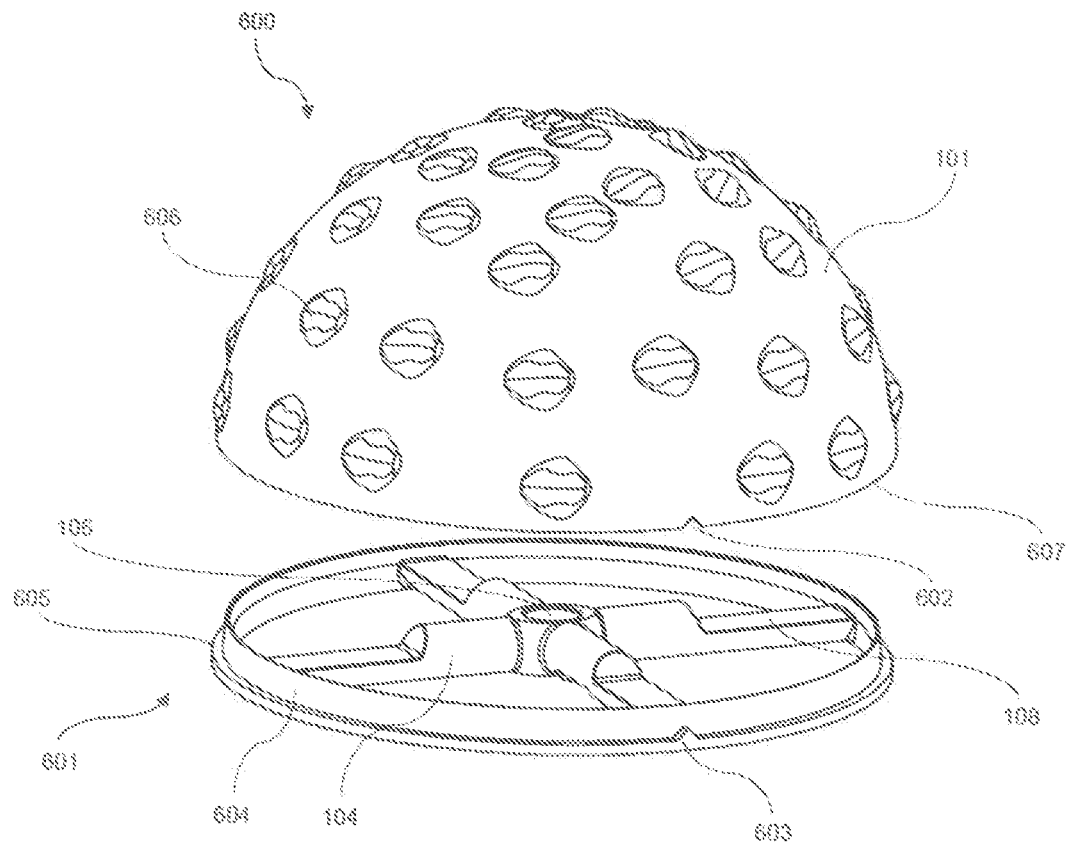
FIG. 6 is an exploded view of the acetabular reamer in a semi-finished state.

Referring now to FIG. 6, the acetabular reamer is shown at an intermediate step of the manufacturing process where the acetabular reamer 100 is composed of two injection molded or 3D-printed pieces, the reamer hollow dome 600 and the reamer connection 601. The reamer connection 601 is preferably made from the same injection molding or 3D-printing process as the reamer hollow dome 600 and assembled together before sintering, welding, or adhering as the case may be, and machining of the holes. The reamer hollow dome 600 has tooth domes 606 that will be used to form the teeth 102. A positioning feature 602, located around the rim 607 of the hollow dome 600, guarantees a correct orientation with the positioning feature 603 of the reamer connection 601 once assembled. The reamer connection 601 has an internal annular rim 604 that will be contacting the domed internal surface 110 once assembled and a base rim 605 that will be contacting the rim 607 of the hollow dome 600 once assembled. Since important internal constraints and deformations may occur during any heat treatment process, the internal annular rim 604 and the base rim 605 may be designed with different shapes, thicknesses and dimensions. The interfacing surfaces may be tapered. The undercuts 108 along the connecting bars 104 are also important for partially reducing the cross-section of the connecting bars and therefore decreasing the internal constraints generated during any heat treatment process and causing eventual deformations of the rim. The undercuts 108 may be replaced by different geometries of the connecting bars 104 allowing an increase or decrease of the cross-section in that area. The hole or opening 106, located at the center of the cross bar (or the reinforcement portion 105) gives direct access to the internal apex surface of the hollow dome. Specific fixtures will be used to support the apex of the hollow dome from the inside during any heat treatment process to avoid its deformation or sagging.

Figure 7:
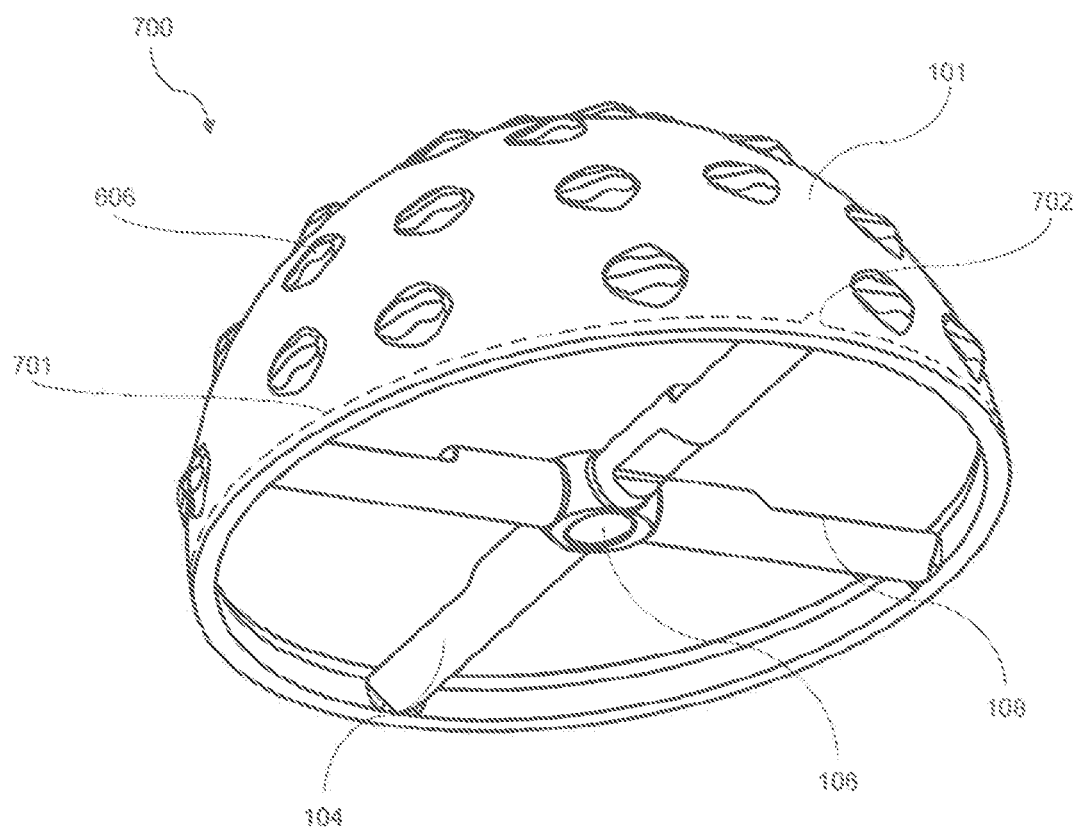
FIG. 7 is a perspective view of the acetabular reamer in a semi-finished state.

Referring now to FIG. 7, the assembly of the reamer hollow dome 600 and the reamer connection 601 is shown. After sintering, welding, adhering using adhesives, or ultrasonic bonding of the assembly 700, the two pieces will be fully fused together, in some cases showing only a parting line 701. The positioning features 602 and 603 are coincident, showing a parting line 702.

Figure 8:
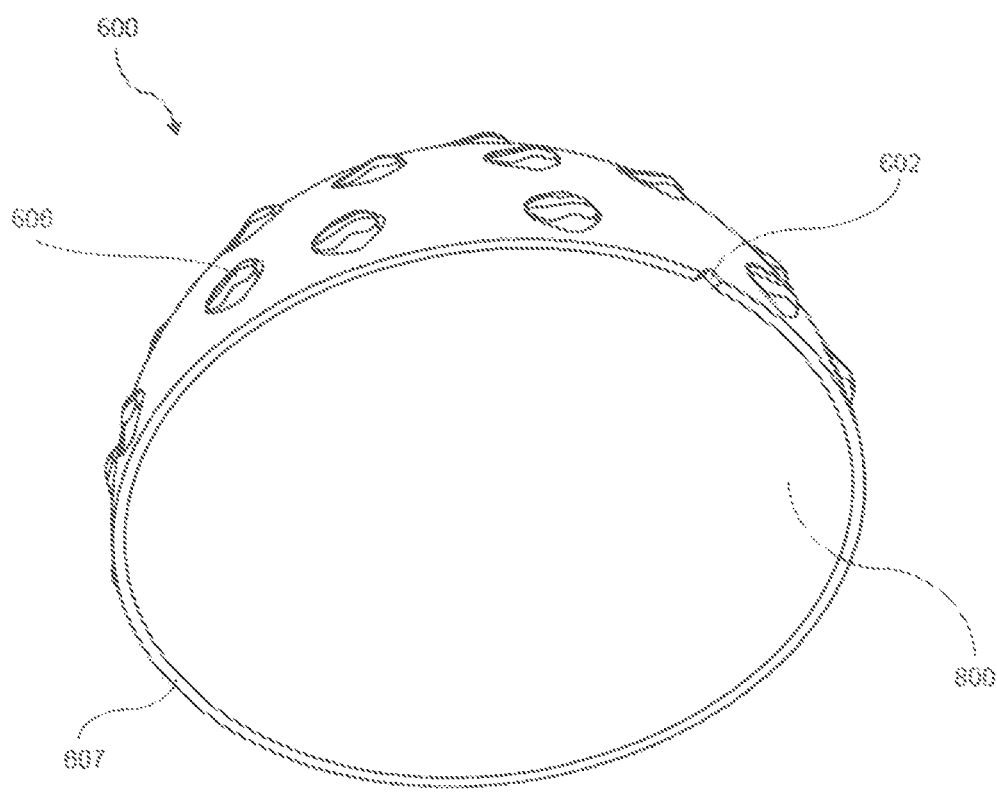
FIG. 8 is a perspective view of the acetabular reamer shell in a semi-finished state.

Referring now to FIG. 8, the reamer hollow dome 600 after injection molding or 3D-printing (and without the reamer connection 601) is shown. The internal surface 800 is smooth.

Figure 9A:
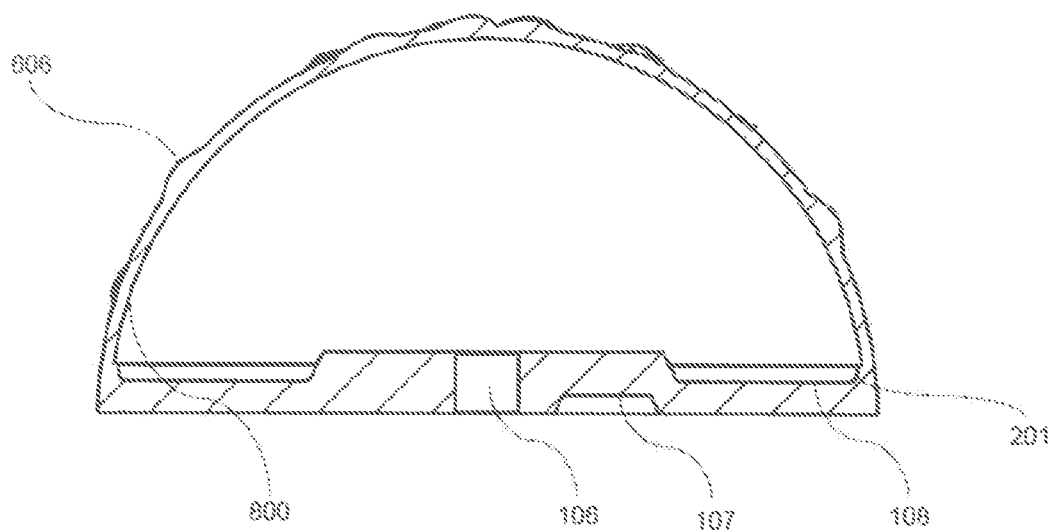
FIG. 9A is a cross-section view of the acetabular reamer in a semi-finished state.
Figure 9B:
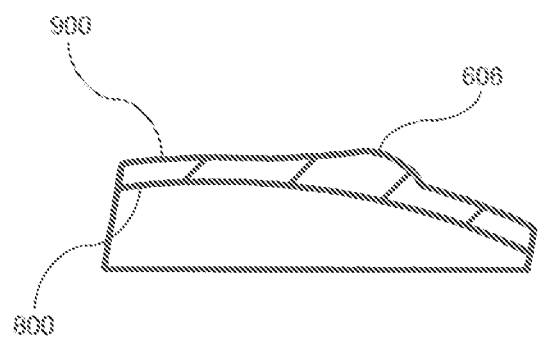
FIG. 9B is a cross-section view of the cutting tooth of the acetabular reamer in a semi-finished state.

Referring now to FIG. 9A, a cross-section of the assembled and optionally heat treated reamer hollow dome 600 and reamer connection 601, where the two pieces will be fully fused together is shown. FIG. 9B, referring as well to a close-up view of the cross-section of a tooth dome is shown prior to drilling or milling of the cutting edge. The thickness of the tooth dome 606 is larger than the thickness of the reamer dome shell.

Figure 10:
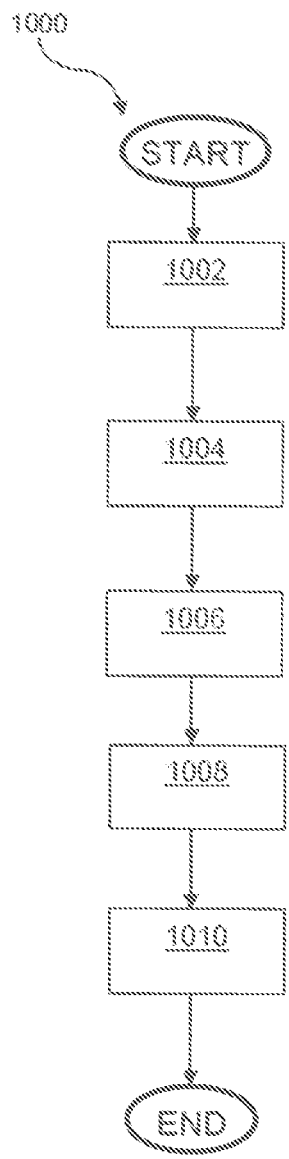
FIG. 10 is a flow chart of the method for manufacturing the acetabular reamer.

Referring now to FIG. 10, the method 1000 for manufacturing the acetabular reamer 100 includes several steps. In a first step 1002, the reamer hollow dome 600 or any portion thereto that when axially rotated (see 121 of FIG. 1C) is configured to cut the bone in a desired fashion, and the reamer connection 601 are made by injection molding or 3D-printing. In a second step 1004, the reamer hollow dome 600 or a portion thereof and the reamer connection 601 are assembled together. A positioning feature 603 insures correct positioning of the two components. In a third step 1006, where injection molding or 3D-printing of a compound of plastic and metal powder is used, the assembly of the two components is sintered at high temperature, which fuses the components together to form only one piece. Alternatively, the components can be adhered, welded, or ultrasonically attached. In a fourth step 1008, tooth holes 109 or a portion thereof are machined into the assembly to create the cutting edges of the teeth. In a fifth step 1010, the assembly is optionally heat treated to give the material the desired hardness properties.

Figure 11:
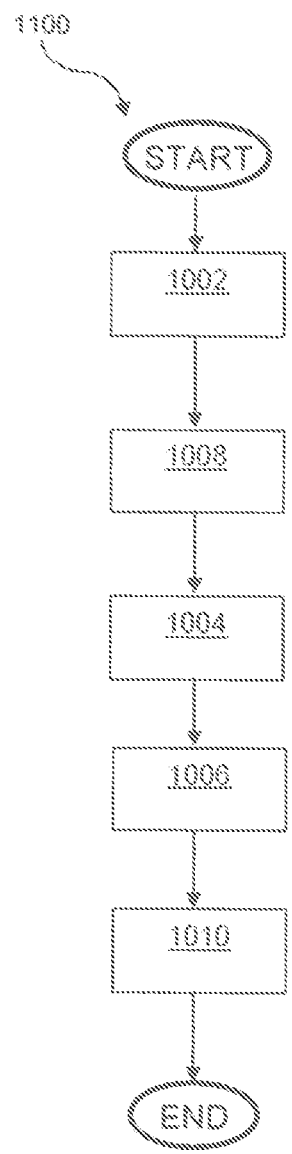
FIG. 11 is a flow chart of a different method for manufacturing the acetabular reamer.

Referring to FIG. 11, an alternative method 1100 for manufacturing the acetabular reamer includes several steps. In a first step 1002, the reamer hollow dome 600 or a portion thereof and the reamer connection 601 are made by injection molding or 3D-printed. In a second step 1008, tooth holes 109 or a portion thereof are machined into the green hollow dome 600 or a portion thereof to create the cutting edges of the teeth. Alternatively, a portion of the tooth holes 109 are formed directly in the mold during the injection molding step or during the 3D-printing step. In a third step 1004, the reamer hollow dome 600 or a portion thereof and the reamer connection 601 are assembled together. A positioning feature 603 insures correct positioning of the two components. In a fourth step 1006, the assembly of the two components is optionally heat treated at high temperature, which fuses the components together to form only one piece. In a fifth step 1010, the part is optionally heat treated to give the material the desired hardness properties.

Importantly, machining the cutting edge after molding or even better after heat treating enables the forming of a more effective cutting tooth with good cutting properties.

The reamer of the invention has at least a portion of a visible parting line.

The invention may be defined as having the following feature sets:

1. A cutting blade comprising a section of a domed external surface and a section of a domed internal surface being concentric about a rotational axis to the section of the domed external surface thereby defining a section of a hollow dome, wherein at least one cutting tooth comprising a cutting edge, a crest and a cutting surface is disposed on the section of the hollow dome and wherein by virtue of the cutting surface having been formed by an injection molding process or a 3D printing process, a cross-sectional thickness T measured substantially perpendicular to the crest of the at least one tooth is greater than a radial distance t between the section of the external and internal domed surfaces, wherein further the section of the external and internal domed surfaces of the section of the hollow dome are interrupted by at least one portion of a hole passing therethrough defining the cutting edge and the cutting surface of the at least one cutting tooth, the cutting edge comprises the crest, wherein the at least one portion of the hole passing therethrough is cylindrical.

2. A cutting blade comprising a section of a domed external surface and a section of a domed internal surface being concentric about a rotational axis to the section of the domed external surface thereby defining a section of a hollow dome, wherein at least one cutting tooth comprising a cutting edge, a crest and a cutting surface is disposed on the section of the hollow dome and wherein by virtue of the cutting surface having been formed by an injection molding process or a 3D printing process, a cross-sectional thickness T measured substantially perpendicular to the crest of the at least one tooth is greater than a radial distance t between the section of the external and internal domed surfaces, wherein further the section of the external and internal domed surfaces of the section of the hollow dome are interrupted by at least one portion of a hole passing therethrough defining the cutting edge and the cutting surface of the at least one cutting tooth, the cutting edge comprises the crest, wherein the at least one portion of the hole passing therethrough is conical and therefore tapered.

3. A cutting blade comprising a section of a domed external surface and a section of a domed internal surface being concentric about a rotational axis to the section of the domed external surface thereby defining a section of a hollow dome, wherein at least one cutting tooth comprising a cutting edge, a crest and a cutting surface is disposed on the section of the hollow dome and wherein by virtue of the cutting surface having been formed by an injection molding process or a 3D printing process, a cross-sectional thickness T measured substantially perpendicular to the crest of the at least one tooth is greater than a radial distance t between the section of the external and internal domed surfaces, wherein further the section of the external and internal domed surfaces of the section of the hollow dome are interrupted by at least one portion of a hole passing therethrough defining the cutting edge and the cutting surface of the at least one portion of the cutting tooth, the cutting edge comprises the crest, the cutting blade further comprising a portion of a visible parting line.

4. A method for manufacturing a cutting blade comprising a section of a hollow dome, the method including the steps of:
 a) injection molding or 3D printing of the section of the hollow dome of the cutting blade including at least one tooth projection;
 b) sintering of the hollow dome of the cutting blade.

5. The method of feature set 4, further including the step of machining of at least one portion of a hole in the at least one tooth projection to create a cutting edge of an at least one tooth.

6. The method of feature set 4, wherein the injection molding is injection molding of metal powder (MIM).

7. The method of feature set 4, wherein the 3D printing is 3D printing of a blend of metal powder and plastic.

8. The method of feature set 4, further including the step of heat treatment of the cutting blade.

9. The cutting blade of feature set 4, wherein a facing surface of the cutting edge is formed or reformed by drilling or milling.

10. A cutting blade comprising a section of a domed external surface and a section of a domed internal surface being concentric about a rotational axis to the section of the domed external surface thereby defining a section of a hollow dome, wherein at least one cutting tooth comprising a cutting edge, a crest and a cutting surface is disposed on the section of the hollow dome and wherein by virtue of the cutting surface having been formed by an injection molding process or a 3D printing process, a cross-sectional thickness T measured substantially perpendicular to the crest of the at least one tooth is greater than a radial distance t between the section of the external and internal domed surfaces, wherein further the section of the external and internal domed surfaces of the section of the hollow dome are interrupted by at least one portion of a hole passing therethrough defining the cutting edge and the cutting surface of the at least one portion of the cutting tooth, the cutting edge comprises the crest, wherein the at least one portion of the hole passing therethrough lacks sharp corners.

11. The cutting blade of feature set 1 further comprising at least a portion of a visible parting line.

12. The cutting blade of feature set 2 wherein the at least one portion of the hole passing therethrough lacks sharp corners.

13. The cutting blade of feature set 2 further comprising at least a portion of a visible parting line.

14. The cutting blade of feature set 3 wherein the at least one portion of the hole passing therethrough lacks sharp corners.

An advantage of the present invention is to provide an acetabular reamer having a smooth surface on its inside, therefore allowing easier cleaning of the instrument. Another advantage of the invention is to improve the accuracy of the positioning and orientation of the teeth by using a more repetitive process with less manual operations. The spherical form of the reamer is also improved because there is no deformation of the shell when punching the teeth, as was the case with prior art reamers.

It should be appreciated that the particular implementations shown and herein described are representative of the invention and its best mode and are not intended to limit the scope of the present invention in any way.

It should be appreciated that many applications of the present invention may be formulated. Moreover, the system contemplates the use, sale and/or distribution of any goods, services or information having similar functionality described herein.

As will be appreciated by skilled artisans, the present invention may be embodied as a system, a device, or a method. Moreover, the system contemplates the use, sale and/or distribution of any goods, services or information having similar functionality described herein.

The specification and figures should be considered in an illustrative manner, rather than a restrictive one and all modifications described herein are intended to be included within the scope of the invention claimed. Accordingly, the scope of the invention should be determined by the appended claims (as they currently exist or as later amended or added, and their legal equivalents) rather than by merely the examples described above. Steps recited in any method or process claims, unless otherwise expressly stated, may be executed in any order and are not limited to the specific order presented in any claim. Further, the elements and/or components recited in apparatus claims may be assembled or otherwise functionally configured in a variety of permutations to produce substantially the same result as the present invention. Consequently, the invention should not be interpreted as being limited to the specific configuration recited in the claims.

Benefits, other advantages and solutions mentioned herein are not to be construed as critical, required or essential features or components of any or all the claims.

As used herein, the terms "comprises", "comprising", or variations thereof, are intended to refer to a non-exclusive listing of elements, such that any apparatus, process, method, article, or composition of the invention that comprises a list of elements, that does not include only those elements recited, but may also include other elements such as those described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention.

The patents and articles mentioned above are hereby incorporated by reference herein, unless otherwise noted, to the extent that the same are not inconsistent with this disclosure.

Further, the invention should be considered as comprising all possible combinations of every feature described in the instant specification, appended claims, and/or drawing figures which may be considered new, inventive and industrially applicable.

Additional features and functionality of the invention are described in the claims appended hereto and/or in the abstract. Such claims and/or abstract are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

The invention claimed is:

1. A cutting blade comprising a section of a domed external surface and a section of a domed internal surface being concentric about a rotational axis to the section of the domed external surface thereby defining a section of a hollow dome, wherein at least one cutting tooth comprising a cutting edge, a crest and a cutting surface is disposed on the section of the hollow dome and wherein by virtue of the cutting surface having been formed by an injection molding process or a 3D printing process, a cross-sectional thickness T measured substantially perpendicular to the crest of the at least one tooth is greater than a radial distance t between the section of the external and internal domed surfaces, wherein further the section of the external and internal domed surfaces of the section of the hollow dome are interrupted by at least one portion of a hole passing therethrough defining the cutting edge and the cutting surface of the at least one cutting tooth, the cutting edge comprises the crest, wherein the at least one portion of the hole passing therethrough is cylindrical.

2. A cutting blade comprising a section of a domed external surface and a section of a domed internal surface being concentric about a rotational axis to the section of the domed external surface thereby defining a section of a hollow dome, wherein at least one cutting tooth comprising a cutting edge, a crest and a cutting surface is disposed on the section of the hollow dome and wherein by virtue of the cutting surface having been formed by an injection molding process or a 3D printing process, a cross-sectional thickness T measured substantially perpendicular to the crest of the at least one tooth is greater than a radial distance t between the section of the external and internal domed surfaces, wherein further the section of the external and internal domed surfaces of the section of the hollow dome are interrupted by at least one portion of a hole passing therethrough defining the cutting edge and the cutting surface of the at least one cutting tooth, the cutting edge comprises the crest, wherein the at least one portion of the hole passing therethrough is conical and therefore tapered.

3. A cutting blade comprising a section of a domed external surface and a section of a domed internal surface being concentric about a rotational axis to the section of the domed external surface thereby defining a section of a hollow dome, wherein at least one cutting tooth comprising a cutting edge, a crest and a cutting surface is disposed on the section of the hollow dome and wherein by virtue of the cutting surface having been formed by an injection molding process or a 3D printing process, a cross-sectional thickness T measured substantially perpendicular to the crest of the at least one tooth is greater than a radial distance t between the section of the external and internal domed surfaces, wherein further the section of the external and internal domed surfaces of the section of the hollow dome are interrupted by at least one portion of a hole passing therethrough defining the cutting edge and the cutting surface of the at least one portion of the cutting tooth, the cutting edge comprises the crest, the cutting blade further comprising a portion of a visible parting line.

4. A method for manufacturing a cutting blade comprising a section of a hollow dome, the method including the steps of:
   a) injection molding or 3D printing of the section of the hollow dome of the cutting blade including at least one tooth projection;
   b) sintering of the hollow dome of the cutting blade.

5. The method of claim 4, further including the step of machining of at least one portion of a hole in the at least one tooth projection to create a cutting edge of an at least one tooth.

6. The method of claim 4, wherein the injection molding is injection molding of metal powder (MIM).

7. The method of claim 4, wherein the 3D printing is 3D printing of a blend of metal powder and plastic.

8. The method of claim 4, further including the step of heat treatment of the cutting blade.

9. The cutting blade of claim 4, wherein a facing surface of the cutting edge is formed or reformed by drilling or milling.

10. A cutting blade comprising a section of a domed external surface and a section of a domed internal surface being concentric about a rotational axis to the section of the domed external surface thereby defining a section of a hollow dome, wherein at least one cutting tooth comprising a cutting edge, a crest and a cutting surface is disposed on the section of the hollow dome and wherein by virtue of the cutting surface having been formed by an injection molding process or a 3D printing process, a cross-sectional thickness T measured substantially perpendicular to the crest of the at least one tooth is greater than a radial distance t between the section of the external and internal domed surfaces, wherein further the section of the external and internal domed surfaces of the section of the hollow dome are interrupted by at least one portion of a hole passing therethrough defining the cutting edge and the cutting surface of the at least one portion of the cutting tooth, the cutting edge comprises the crest, wherein the at least one portion of the hole passing therethrough lacks sharp corners.

11. The cutting blade of claim 1 further comprising at least a portion of a visible parting line.

12. The cutting blade of claim 2 wherein the at least one portion of the hole passing therethrough lacks sharp corners.

13. The cutting blade of claim 2 further comprising at least a portion of a visible parting line.

14. The cutting blade of claim 3 wherein the at least one portion of the hole passing therethrough lacks sharp corners.

* * * * *